United States Patent [19]

Merger et al.

[11] 4,320,235

[45] Mar. 16, 1982

[54] PREPARATION OF 1-(ARALKYL)-2-NAPHTHOLS

[75] Inventors: Franz Merger, Frankenthal; Gerhard Nestler, Ludwigshafen, both of Fed. Rep. of Germany

[73] Assignee: BASF Aktiengesellschaft, Fed. Rep. of Germany

[21] Appl. No.: 209,280

[22] Filed: Nov. 21, 1980

[30] Foreign Application Priority Data

Dec. 14, 1979 [DE] Fed. Rep. of Germany ....... 2950290

[51] Int. Cl.$^3$ ....................... C07C 39/12; C07C 39/14
[52] U.S. Cl. .................................... 568/736; 568/735; 568/744; 568/733
[58] Field of Search ............... 568/735, 736, 733, 744, 568/731

[56] References Cited

U.S. PATENT DOCUMENTS 2,714,120  7/1955  Kehe .

FOREIGN PATENT DOCUMENTS 1099350  9/1961  Fed. Rep. of Germany .
1111751  5/1968  United Kingdom ................ 568/744
330151  4/1962  U.S.S.R. ............................. 568/744

OTHER PUBLICATIONS

J. Org. Chem. 17 (1952), pp. 1019–1020.
J. Org. Chem. 17 (1951), pp. 185–191.
Chemistry Letters (1975), pp. 1019–1020

*Primary Examiner*—Werren B. Lone
*Attorney, Agent, or Firm*—Keil & Witherspoon

[57] ABSTRACT

1-(Aralkyl)-2-naphthols are prepared by reacting a 2-naphthol with a styrene in the presence of a carboxylic acid.

The 1-(aralkyl)-2-naphthols obtainable by the process according to the invention are valuable starting materials for the preparation of dyes, pest control agents, drugs, ointments, emulsifiers, dispersants, stabilizers, hydraulic fluids, plasticizers, corrosion inhibitors, disinfectants, crop protection agents and scents.

6 Claims, No Drawings

PREPARATION OF 1-(ARALKYL)-2-NAPHTHOLS

The present invention relates to a process for the preparation of 1-(aralkyl)-2-naphthols by reacting a 2-naphthol with a styrene in the presence of a carboxylic acid.

1-Alkylated and 1-benzylated 2-naphthols have hitherto been prepared in the main by reaction of an alkali metal naphtholate with an alcohol at a high temperature, or by multi-stage syntheses, the yields being moderate (Chemistry Letters 1975, pages 1,019 to 1,020).

U.S. Pat. No. 2,714,120 describes the preparation of 1-(aralkyl)-2-naphthols by reacting a 2-naphthol with a styrene in the presence of dilute sulfuric acid or of a sulfonic acid, especially p-toluenesulfonic acid, the yield being 16.5 percent.

It is known that as a rule the alkylation of 2-naphthol with an olefin or alcohol in the presence of an inorganic acid or organic sulfonic acid principally gives a 6-alkylated 2-naphthol. J. Org. Che., 17 (1952), 243- 248 describes the preparation of 6-($\alpha$-phenylethyl)-2-naphthol by reacting 2-naphthol with styrene in the presence of sulfuric acid, the yield being 92 percent. J. Org. Chem., 16 (1951), 185-191 discloses that 6-cyclohexyl-2-naphthol is formed by reacting 2-naphthol with cyclohexanol in the presence of phosphoric acid.

We have found that 1-(aralkyl)-2-naphthols of the formula

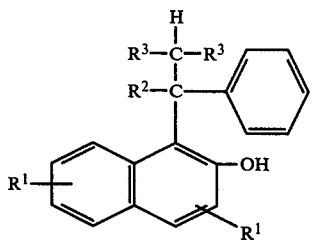

where the individual radicals $R^1$, $R^2$ and $R^3$ may be identical or different and each is hydrogen or an aliphatic radical, and $R^1$ may also be alkoxy or halogen, are obtained in an advantageous manner by reacting a naphthol with an olefin in the presence of an acid, if a 2-naphthol of the formula

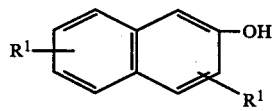

where $R^1$ has the above meanings, is reacted with a styrene of the formula

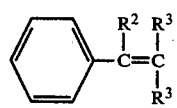

where $R^2$ and $R^3$ have the above meanings, in the presence of a carboxylic acid.

Where styrene and 2-naphthol is used, the reaction may be represented by the following equation:

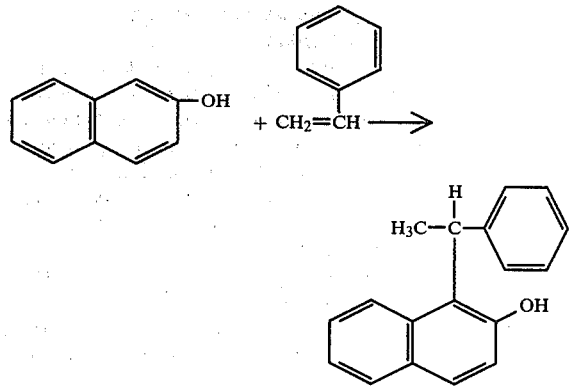

Compared to the conventional processes, the process according to the invention surprisingly gives 1-(aralkyl)-2-naphthols more simply and more economically, with a better space-time yield and in greater purity. The reaction mixture can advantageously be worked up directly by distillation, without separating off the catalyst.

The starting materials are reacted in the stoichiometric ratio or in excess, preferably in a ratio of from 0.5 to 2, advantageously from 0.8 to 1.2, moles of starting material III per mole of naphthol II. Preferred starting materials II and III and accordingly preferred end products I are those where the individual radicals $R^1$, $R^2$ and $R^3$ are identical or different and each is hydrogen or alkyl of 1 to 8, especially of 1 to 4, carbon atoms, and $R^1$ may also be alkoxy of 1 to 8, especially of 1 to 4, carbon atoms, chlorine or bromine. The said radicals may additionally be substituted by groups which are inert under the reaction conditions, for example alkyl or alkoxy of 1 to 4 carbon atoms.

The following naphthols are examples of suitable starting materials II: chloro-, bromo-, methyl-, ethyl-, n-propyl-, isopropyl-, n-butyl-, isobutyl- and sec.-butyl$\beta$-naphthol, the halogen or alkyl substituent being in the 3-, 4-, 5-, 6-, 7- or 8-position; methyl, ethyl, n-propyl, n-butyl and isobutyl ethers of $\beta$-naphthols which have a further hydroxyl in the above positions; $\beta$-naphthol disubstituted in the 3,4-, 4,5-, 4,6- and 6,7-positions by chlorine, bromine, methyl, ethyl, n-propyl, isopropyl, n-butyl, isobutyl or sec.-butyl; and corresponding $\beta$-naphthols with 2 different radicals from amongst those mentioned above, eg. 4-ethyl-6-chloro-2-naphthol and 3-methyl-4-methyoxy-2-naphthol. $\beta$-Naphthol itself is however preferred.

The following are examples of styrenes which may be used as starting materials III: styrene itself and styrenes which are monosubstituted in the $\alpha$- or $\beta$-position, or have two identical or different substitutents in the $\alpha,\beta$- or $\beta,\beta$-positions or have three identical or different substituents in the $\alpha,\beta,\beta$-positions, the substituents being methyl, ethyl, propyl, isopropyl or butyl.

The reaction is in general carried out at from 100° to 180° C., preferably from 120° to 150° C., under reduced, atmospheric or superatomospheric pressure, batchwise or continuously. Advantageously, no added solvent is used; however, solvents which are inert under the reaction conditions may be employed where appropriate, for example to lower the viscosity of the reaction mixture. Examples of suitable solvents are halohydrocarbons, especially chlorohydrocarbons, eg. tetrachloroethylene, 1,1,2,2-tetrachloroethane or 1,1,1,2-tetrachloroethane, dichloropropane, methylene chloride, dichlorobutane, chloroform, carbon tetrachloride, tetrachloroethane, 1,1,1-trichloroethane or 1,1,2-trichloroethane, trichloroethylene, pentachloroethane, 1,2-dichloroethane and 1,1-dichloroethane; tetrahydrofuran and dioxane; aromatic hydrocarbons, eg. toluene, ethylbenzene, o-, m- and p-xylene, isopropylbenzene, chlorobenzene and methylnaphthalene; and mixtures of the above. Advantageously, the solvent is used in an amount of from 10 to 1,000, preferably from 50 to 100, percent by weight, based on olefin III.

Suitable carboxylic acids may be araliphatic, aromatic or, preferably, aliphatic, and either polybasic, advantageously dibasic, or particularly advantageously, monobasic. The carboxylic acids advantageously have a dissociation exponent $pK_a$ of less than 5, preferably of from 0.1 to 4, especially from 0.1 to 2. Preferred acids have the formula

where $R^4$ is hydrogen, alkyl of 1 to 8, especially of 1 to 4, carbon atoms, which is unsubstituted or substituted by chlorine, fluorine, cyano, nitro and/or an additional carboxyl, alkylphenyl of 7 to 12 carbon atoms, or phenyl. The above radicals may in addition be substituted by groups and/or atoms which are inert under the reaction conditions, for example bromine, chlorine, alkyl of 1 to 4 carbon atoms, cyano, carboxyl, carbalkoxy, acetyl or nitro. The carboxylic acid is preferably used in an amount of from 0.01 to 1, especially from 0.005 to 0.5, equivalent per mole of starting material II.

Examples of suitable carboxylic acids are the following: aliphatic carboxylic acids, eg. chloroacetic acid, dichloroacetic acid, trichloroacetic acid, oxalic acid, formic acid, cyanoacetic acid, acetic acid, trifluoroacetic acid, monobromoacetic acid, α-chloropropionic acid, malonic acid, α,α-dichloropropionic acid and aromatic carboxylic acids, eg. benzoic acid, 2,3-, 2,4-, 2,5- and 2,6-dichlorobenzoic acid, o-, m- and p-chlorobenzoic acid, phthalic acid and o-, m- and p-nitrobenzoic acid. Dichloroacetic acid, trichloroacetic acid, trifluoroacetic acid and oxalic acid are preferred.

The reaction may be carried out as follows: a mixture of the starting materials II and III, the carboxylic acid and the solvent, if any, is kept at the reaction temperature for from 2 to 5 hours. The end product is then isolated from the reaction mixture in a conventional manner, for example by distillation.

The 1-(aralkyl)-2-naphthols I obtainable by the process of the invention are valuable starting materials for the preparation of dyes, pest control agents, drugs, ointments, emulsifiers, dispersants, stabilizers, hydraulic fluids, plasticizers, corrosion inhibitors, disinfectants, crop protection agents and scents. 1-Aralkylated 2-naphthols are used as couplers in color photography (German Published Application DAS No. 1,099,350). Concerning the use of the compounds, reference may be made to the publications mentioned above.

In the Examples which follow, parts are by weight.

EXAMPLE 1

Using a stirred reactor, a mixture of 144 parts of 2-naphthol and 5 parts of oxalic acid is heated to 130° C., while stirring, and 104 parts of styrene are added continuously over one hour. The mixture is then stirred for three hours at 130° C. After completion of the reaction, the mixture is distilled under reduced pressure, giving 213 parts (86% of theory) of 1(α-phenylethyl)-2-naphthol (boiling point 172/176° C./0.2 mbar). The conversion is 90 percent.

COMPARATIVE EXAMPLE 2

Using a stirred reactor, a mixture of 144 parts of 2-naphthol and 1 part of 96 percent strength by weight sulfuric acid is heated to 120° C., whilst stirring, and 104 parts of styrene are fed in continuously over two hours. The mixture is then stirred for two hours at 120° C. According to analysis by gas chromatography, the reaction mixture consists of 12 percent by weight of 2-naphthol, 42 percent by weight of 6- and 3-(α-phenylethyl)-2-naphthol (in the ratio of 1:1) and 6 percent by weight of dinaphthyl ether, the remainder being di-alkylated and more highly alkylated naphthols.

COMPARATIVE EXAMPLE 3

Using a stirred reactor, a mixture of 144 parts of 2-naphthol and 4 parts of 85 percent strength by weight phosphoric acid is heated to 120° C., whilst stirring, and 104 parts of styrene are fed in continuously over two hours. The mixture is then stirred for two hours at 120° C. According to analysis by gas chromatography, the reaction mixture consists of 6 percent by weight of 2-naphthol, 37 percent by weight of 1-(α-phenylethyl)-2-naphthol and 46 percent by weight of 6- and 3-(αphenylethyl)-2-naphthol (in the ratio of 1:1), the remainder being dialkylated and more highly alkylated naphthols.

We claim:

1. A process for the preparation of 1-(aralkyl)-2-naphthols of the formula

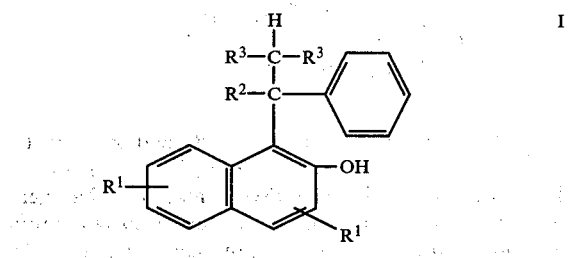

where the individual radicals $R^1$, $R^2$ and $R^3$ may be identical or different and each is hydrogen or an aliphatic radical, and $R^1$ may also be alkoxy or halogen, by reacting a naphthol with an olefin in the presence of an acid wherein a 2-naphthol of the formula

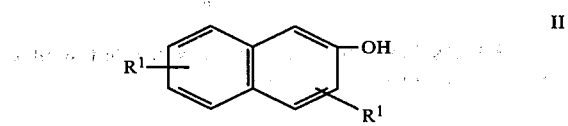

where $R^1$ has the above meanings, is reacted with a styrene of the formula

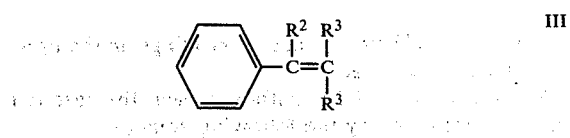

where $R^2$ and $R^3$ have the above meanings, in the presence of a carboxylic acid of the formula

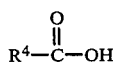   IV where $R^4$ is hydrogen, alkyl of 1 to 8 carbon atoms, which is unsubstituted or substituted by chlorine, fluorine, cyano, nitro and/or an additional carboxyl, alkylphenyl of 7 to 12 carbon atoms, or phenyl, the above radicals being unsubstituted or substituted by bromine, chlorine, alkyl of 1 to 4 carbon atoms, cyano, carboxyl, carbalkoxy, acetyl or nitro.

2. A process as claimed in claim 1, wherein the reaction is carried out with from 0.5 to 2 moles of startig material III per mole of naphthol II.

3. A process as claimed in claim 1, wherein the reaction is carried out at from 100° to 180° C.

4. A process as claimed in claim 1, wherein the reaction is carried out at from 120° to 150° C.

5. A process is claimed in claim 1, wherein the reaction is carried out with a carboxylic acid having a dissociation exponent $pK_a$ of less than 5.

6. A process as claimed in claim 1, wherein the reaction is carried out with from 0.01 to 1 equivalent of carboxylic acid per mole of starting material II.

* * * * *